US006309876B1

(12) United States Patent
Miller et al.

(10) Patent No.: US 6,309,876 B1
(45) Date of Patent: *Oct. 30, 2001

(54) NEURON PROMOTER AND USES

(75) Inventors: Freda Diane Miller; Andrew Gloster; Carrie Grace Causing, all of Montréal; Jean George Toma, Edmonton, all of (CA)

(73) Assignee: McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/460,635

(22) Filed: Dec. 14, 1999

Related U.S. Application Data

(62) Division of application No. 08/215,083, filed on Mar. 18, 1994, now Pat. No. 5,661,032, and a continuation of application No. 08/900,026, filed on Jul. 24, 1997, now Pat. No. 6,000,772.

(51) Int. Cl.[7] .............................. C12N 15/00; C12N 5/00; C12Q 1/02; C07H 21/04
(52) U.S. Cl. ..................... 435/320.1; 435/29; 435/325; 435/455; 536/24.1
(58) Field of Search ................. 536/24.1; 435/320.1, 435/29, 325, 455

(56) References Cited

U.S. PATENT DOCUMENTS

| | | |
|---|---|---|
| 5,087,571 | 2/1992 | Leder et al. . |
| 5,661,032 * | 8/1997 | Miller et al. ................ 435/320.1 |
| 6,000,772 * | 12/1999 | Miller et al. ................... 435/29 |

FOREIGN PATENT DOCUMENTS

| | | |
|---|---|---|
| WO-A93/07280 | 4/1993 | (WO) . |
| WO 94/04695 | 3/1994 | (WO) . |

OTHER PUBLICATIONS

Brown, TINS 1:10–14 (1984).
Cowan et al., Mol. Cell. Biol. 3:1738–1745 (1983).
Daniels, J. Cell. Biol. 53:164–176 (1972).
Ginzburg et al., Nucleic Acid Res. 9:2691–2697 (1986).
Lemischka and Sharp, Nature 300:300–155 (1982).
Lemischka et al., J. Mol. Biol. 150:101–120 (1981).
Lewis et al., J. Cell. Biol. 101:852–861 (1985).
Ma et al., J. Cell. Biol. 117:135–141 (1992).
Mathew and Miller, Dev. Biol. 141:84–92 (1990).
Mathew and Miller, Dev. Biol. 158:467–474 (1993).
Mercer et al., Neuron 7:703–716 (1991).
Miller et al., J. Cell. Biol. 105:3065–3073 (1987).
Miller et al., J. Neurosci. 9:1452–1463 (1989).
Purves et al., J. NeuRosci. 6:1051–1060 (1986).
Tetzlaff et al., J. Neurosci. 11:2528–2544 (1991).
Villasante et al., Mol. Cell. Biol. 6:2409–2419 (1986).
Wang et al., J. Cell. Biol. 103:1903–1910 (1986).
Wu et al., Dev. Biol., 158:456–466 (1993).
Miller et al., Society for Neuroscience Abstracts, 18(1–2):1332 (1992).
Toma et al., Society for Neuroscience Abstracts, 18(1–2):1332 (1992).
Gloster et al., Society for Neuroscience Abstracts 19(1–3):1081 (1993).
Mercer et al., Neuron 7(5):703–716 (1991).
Gloster et al., J. of Cell. Biochem. Suppl. 0(19B):132 (1995).
Gloster et al., J. of Neuroscience 14(12):7319–7330 (1994).
Rogers et al., Society for Neuroscience Abstracts 20(1–2):1488 (1994).
Gloster et al., Society for Neuroscience Abstracts 20(1–2) (1994).
Kappel et al., Current Op. Biotech 3:548–553 (1992).
Wall, Theriogenology 45:57–68 (1996).
Blau et al., The New Eng. J. Med., 1204–1207 (Nov. 2, 1995).
Mueligin, Science 260:926–932 (1993).
Science News Report, Science 269:1050–1055 (1995).
Anderson, Human Gene Therapy 5:281–282 (1994).

* cited by examiner

*Primary Examiner*—Deborah Crouch
(74) *Attorney, Agent, or Firm*—Clark & Elbing, LLP

(57) ABSTRACT

The present invention relates to a DNA expression vector comprising a Tα1 α-tubulin promoter operatively linked upstream to a marker gene sequence relative to the direction of transcription in a eukaryotic expression vector adapted to be introduced into a mammal, or ancestor of the mammal at an embryonic stage and the promoter is controlling transcription of the marker gene. The present invention also relates to a method for testing material suspected of promoting neurogenesis and neuronal growth which comprises exposing a transgenic mammal according to the present invention to the material and detecting the expressed marker gene as an indication of neurogenesis and neuronal growth.

4 Claims, 8 Drawing Sheets

```
                                                                       ERE
  -1028  GTATCCAGACTCACTCCTTTCTCCTTACAGTTTCTGAATTCCGTATTAGAAGGGATGGCTCATTTCTAGGGACAAAAT

NF-IL6
  - 950  AACACAGGCTCTGGGGTGAGGTAGGGTCGGGTAAGGGGGCGAGCGGGGAGGGGTGATGGAAGAGCACTACCGCATAAA

VGF/PERIPHERIN
  - 872  GAAAGCAAGCTCTCTAGTAAAGCGTTAAGTACTACTTTGTATATTGTTTCTCTTTTTTCCTTTCTCTCTCTCTCTCTC

- 794  TTTGTTTGTTTTTGGTTTTTGAGACAGAATATCACACTATATATCCAGGCCGGGTACAAAATAACCGCAGTCCTCCGC

ERE          GAMMA-IRE
  - 716  TTCCCAATGCTGGGATTTACAGGCATAAACCACTAAGGGCGGTTATGATGACCTTGAGCTGCAAGTCTTCCTGCCTCT
                                                SP1          RARE
               E-BOX       RARE                                          HOMEODOMAIN
  - 638  GCCTCCCAGGTGCTGTTGAGGGTCATAGGCGTGGTCTATTCATACTGAGCTTCTGAATTTGCTCAAATATTAATAATA

E-BOX                 AP-2         RARE
  - 560  ATAGTAATAATAATAATAACCACAATAATACAACTGTAAAACTAAACATTTACCCACGCCTTTTTGACCATCATTCCC

GAMMA-IRE
  - 482  ATAGCTCTTGCTACTTTATTTAAAGCGAACAGAGATGTTGAATCCTGACGGAACGTATTTAAATTTAGTGTAGTATAA

GAMMA-IRE
  - 404  ATGAAAAGCTGGAATTTACCATAAAGAATCTCAACACAAATTCTGTGATTAAGTGTTGGGGAAAACCTTAAATTATCC

AP-2        bα1            AP-2
  - 326  TAACTACAGTTTAAGGTTTAAGCTCCGTATAATCACCCAACCCCGTTTTCTTTCTTCCCTCTCTACCCCTCCCCAGC
                                                       VGF/PERIPHERIN
                         AP-2
  - 248  TCCACCCCATAATGGATGCTCGGCTAGTTGCTTTTGCGAGGCCTTTGTCTGAAGGATGCAAAATCTACGGATGCTAGC

C/EBP
  - 170  GAGGGGGGGAAGGGGGGAGAGATTACCTCATACCATGTCGCTTGCACCAATCACCACTCCTGTCGCGGCTTCTCTGGG

PEA-3       AP-2       RARE       TATAA
  - 92   CAGACGGAGGGGTCTGGACCAACAGGAAAAGGCCTTGGCCCATCCCCATGGTGACCGAGCTGTATATAAGGAGGCGCA

5' UT
  - 14   TCCGCCCAAGTGCC          GGCAGGTTCTCTTACATCGACCGCTTAAGAGTCGCGCTGTAAGAAGCAACACC

Met  IVS1
  + 54   TCCTCCTCGCCTCCGCCATCCACCCGGCAGCCGCGAAGCAGCAACC  ATG  GTGAGCAAAC
```

FIG. 1

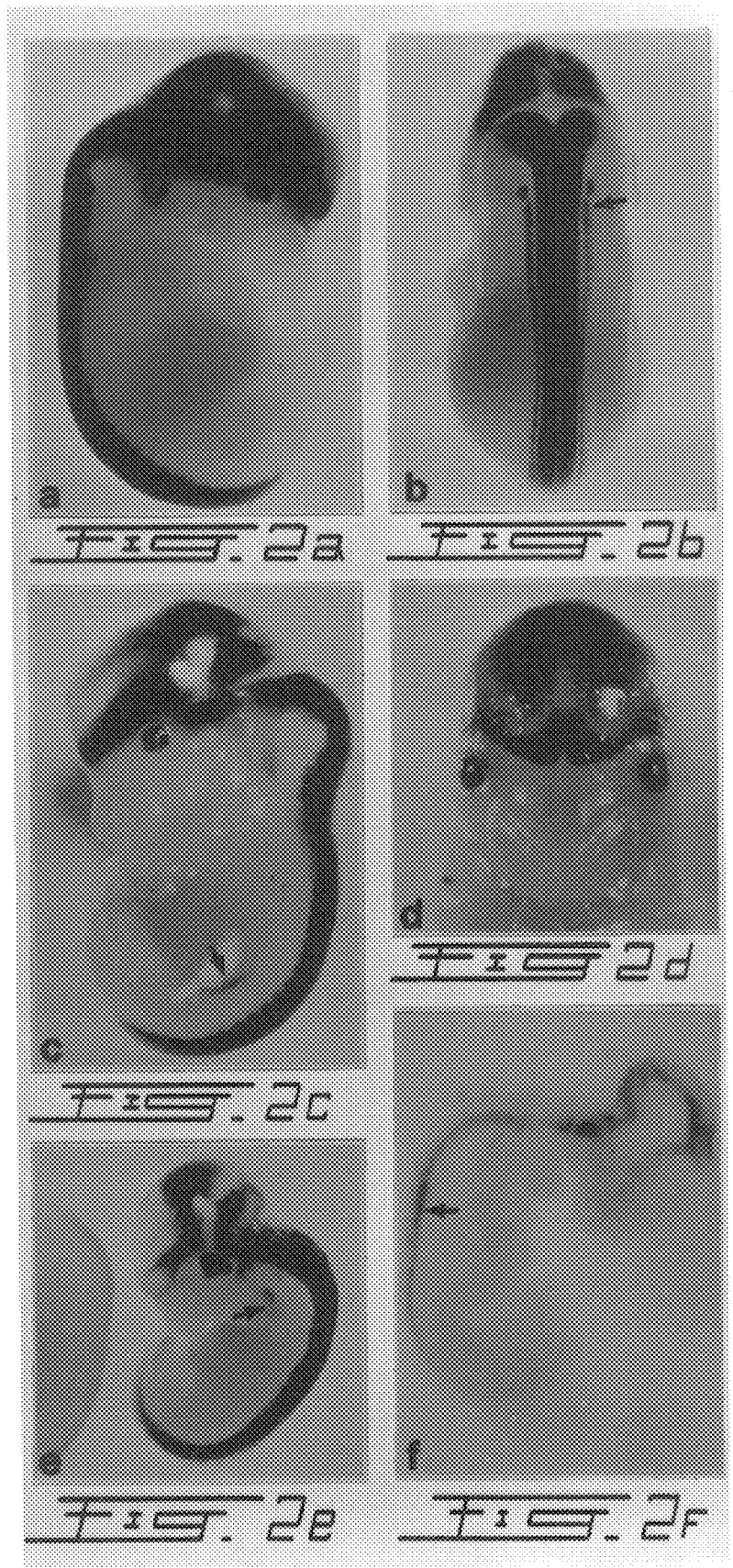

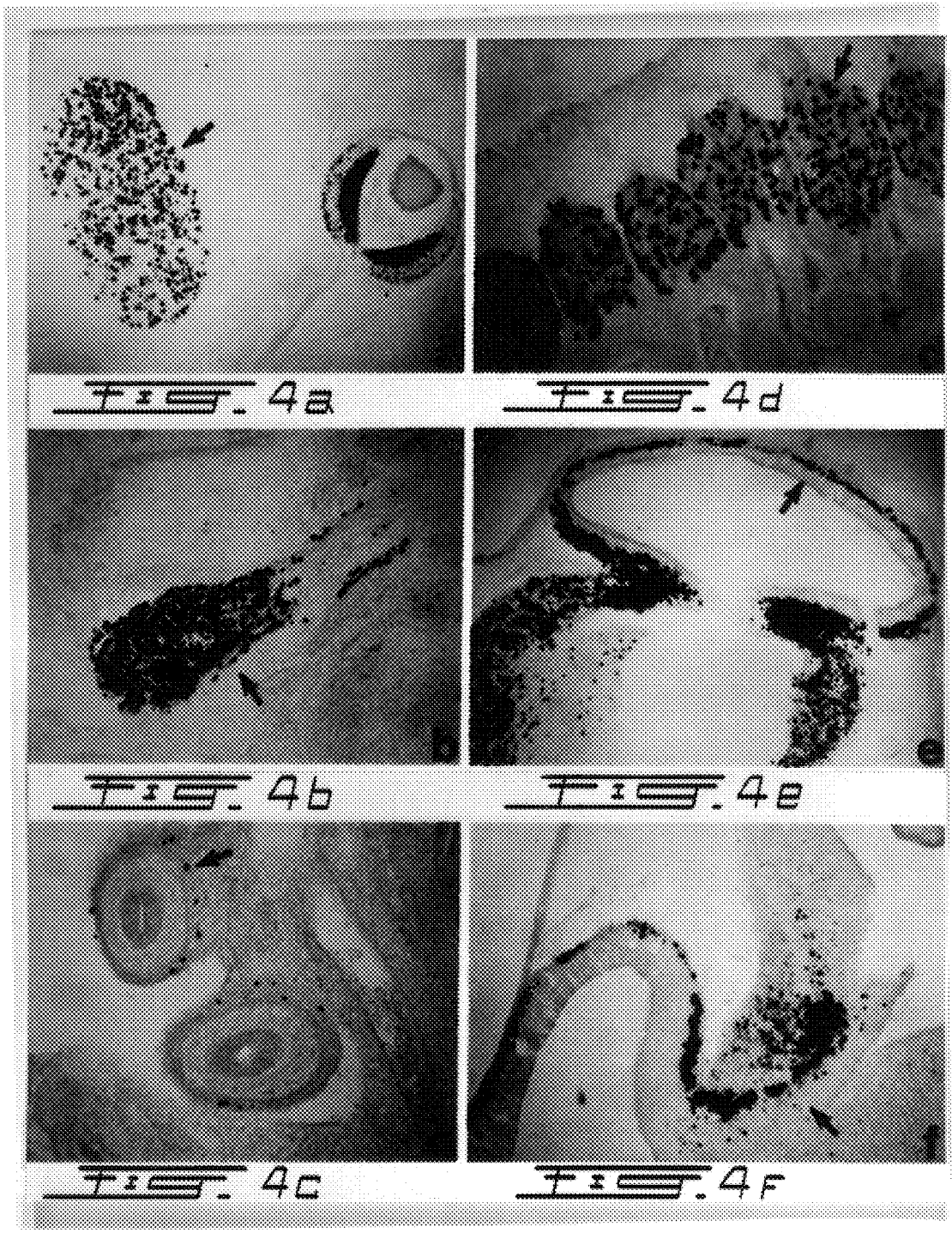

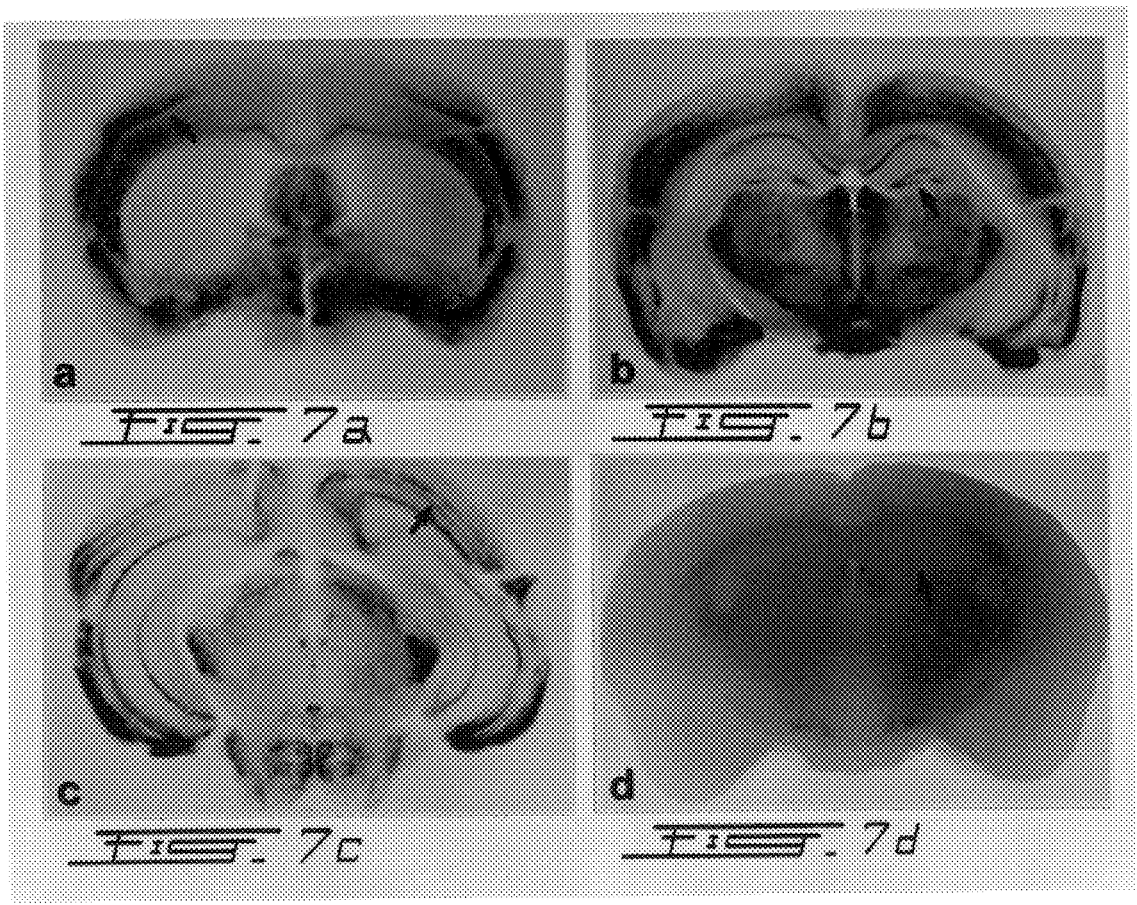

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1157 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GTATCCAGAC TCACTCCTTT CTCCTTACAG TTTCTGAATT CCGTATTAGA AGGGATGGCT      60

CATTTCTAGG GACAAAATAA CACAGGCTCT GGGGTGAGGT AGGGTCGGGT AAGGGGGCGA     120
```

-continued

```
GCGGGGAGGG GTGATGGAAG AGCACTACCG CATAAAGAAA GCAAGCTCTC TAGTAAAGCG      180

TTAAGTACTA CTTTGTATAT TGTTTCTCTT TTTTCCTTTC TCTCTCTCTC TCTCTTTGTT      240

TGTTTTTGGT TTTTGAGACA GAATATCACA CTATATATCC AGGCCGGGTA CAAAATAACC      300

GCAGTCCTCC GCTTCCCAAT GCTGGGATTT ACAGGCATAA ACCACTAAGG GCGGTTATGA      360

TGACCTTGAG CTGCAAGTCT TCCTGCCTCT GCCTCCCAGG TGCTGTTGAG GGTCATAGGC      420

GTGGTCTATT CATACTGAGC TTCTGAATTT GCTCAAATAT TAATAATAAT AGTAATAATA      480

ATAATAACCA CAATAATACA ACTGTAAAAC TAAACATTTA CCCACGCCTT TTTGACCATC      540

ATTCCCATAG CTCTTGCTAC TTTATTTAAA GCGAACAGAG ATGTTGAATC CTGACGGAAC      600

GTATTTAAAT TTAGTGTAGT ATAAATGAAA AGCTGGAATT TACCATAAAG AATCTCAACA      660

CAAATTCTGT GATTAAGTGT TGGGGAAAAC CTTAAATTAT CCTAACTACA GTTTAAGGTT      720

TAAGCTCCGT ATAATCACCC AACCCCCGTT TTCTTTCTTC CCTCTCTACC CCTCCCCAGC      780

TCCACCCCAT AATGGATGCT CGGCTAGTTG CTTTTGCGAG GCCTTTGTCT GAAGGATGCA      840

AAATCTACGG ATGCTAGCGA GGGGGGGAAG GGGGGAGAGA TTACCTCATA CCATGTCGCT      900

TGCACCAATC ACCACTCCTG TCGCGGCTTC TCTGGGCAGA CGGAGGGGTC TGGACCAACA      960

GGAAAAGGCC TTGGCCCATC CCCATGGTGA CCGAGCTGTA TATAAGGAGG CGCATCCGCC     1020

CAAGTGCCGG CAGGTTCTCT TACATCGACC GCTTAAGAGT CGCGCTGTAA GAAGCAACAC     1080

CTCCTCCTCG CCTCCGCCAT CCACCCGGCA GCCGCGAAGC AGCAACCATG GTGAGCAAAC     1140

GAGCGGGGAA AAGGGAG                                                    1157
```

NEURON PROMOTER AND USES

CROSS-REFERENCE TO RELATED APPLICATIONS

This application is a divisional of U.S. Ser. No. 08/215,083, filed Mar. 18, 1994, now U.S. Pat. No. 5,661,032 and is a continuation of U.S. Ser. No. 08/900,026, filed Jul. 24, 1997, now U.S. Pat. No. 6,000,772.

BACKGROUND OF THE INVENTION (a) Field of the Invention

The invention relates to an isolated and characterized neuron promoter serving as a neurogenesis and neuronal differentiation marker and for use in transgenic mammals.

(b) Description of Prior Art

Neurons are highly polarized cells whose most obvious feature is their extensive system of axons and dendrites. This complex morphology is elaborated during embryogenesis and early postnatal life in mice, and likely involves a complex interplay between extrinsic influences and intrinsic neuronal genetic mechanisms. New morphological growth also occurs in the mature nervous system in response to neural trauma or pathology (Brown, 1984, TINS, 1:10–14), and may be an ongoing phenomena in the normal, mature animal (Purves et al., 1986, J. Neurosci., 6:1051–1060). The biological importance of such structural plasticity largely derives from the fact that, neurons of the mature nervous system neither develop de novo nor migrate to new positions in substantial numbers. Thus, the growth and remodeling of mature neurons provides the nervous system with one potential cellular mechanism for responding to ongoing physiological and/or pathological phenomena. The molecular mechanisms underlying morphological growth, and the extraneuronal cues that regulate it remain largely undefined.

Microtubules, which are assembled from α- and βtubulins, comprise the major cytoskeletal component of growing neurites (Daniels, 1972, J. Cell. Biol., 53:164–176). In mammals, at least 6 different α-tubulin genes (Villasante et al., 1986, Mol. Cell. Biol., 6:2409–2419) and 5 different β-tubulin genes (Wang et al., 1986, J. Cell. Biol., 103:1903–1910) are expressed in neural and nonneural tissues at various times during development. It has been previously demonstrated that, of two α-tubulin genes known to be expressed in the embryonic nervous system of the rat, one, termed Tα1, is abundantly expressed in developing neurons during morphological growth, while a second, termed T26, is constitutively expressed in neurons and nonneuronal cells (Miller et al., 1987, J. Cell. Biol., 105:3065–3073). Moreover, it is likely that the Tα1 isotype is incorporated in the majority of neuronal microtubules during development, since Tα1 mRNA comprises 1–2% of the total mRNA, and >95% of the total α-tubulin mRNA in the embryonic nervous system.

Expression of Tα1 α-tubulin mRNA is also correlated with the growth of mature neurons. Following axotomy of motor (Miller et al., 1989, J. Neurosci., 9:1452–1463), and sympathetic (Mathew and Miller, 1993, Dev. Biol., 158:467–474; Wu et al., 1993, Dev. Biol., 158:456–466) neurons, Tα1 mRNA increases rapidly, peaks at 3 to 7 days postlesion, and decreases to control levels following target reinnervation. If regeneration is unsuccessful, as with central nervous system (CNS) neurons (Tetzlaff et al., 1991, J. Neurosci., 11:2528–2544), or with transection of peripheral neurons (Miller et al., 1989, J. Neurosci., 9:1452–1463), Tα1 mRNA levels remain-elevated. These increases appear to be due, to a great extent, to loss of repressive homeostatic signals arising from the non-terminal axon (Mathew and Miller, 1990, Dev. Biol., 141:84–92). Tα1 α-tubulin mRNA levels are also increased during collateral sprouting of adult sympathetic neurons (Mathew and Miller, 1990, Dev. Biol., 141:84–92), presumably in response to increased target-derived nerve growth factor (NGF), since exogenous NGF can increase Tα1 α-tubulin mRNA levels in these neurons both in vivo and in culture (Ma et al,. 1992, J. Cell. Biol., 117:135–141). Thus, expression of Tα1 mRNA is high during developmental growth, is down-regulated as a function of neuronal maturation, and is then increased in response to extrinsic cues that regulate the growth of mature neurons.

The functional role of these high levels of expression of one particular α-tubulin isotype during neuronal growth remains speculative. The rat Tα1, human bα1, and mouse Mα1 α-tubulin mRNAs all encode identical proteins and share 82% homology in their 3' noncoding regions (Lemischka et al., 1981, J. Mol. Biol., 150:101–120). Although the rat T26 mRNA sequence is not complete (Ginzburg et al., 1986, Nucleic Acid Res., 9:2691–2697), the defined amino acid sequence is identical to that shared by human kα1 (Cowan et al., 1983, Mol. Cell. Biol., 3:1738–1745), and mouse Mα1 (Lewis et al., 1985, J. Cell. Biol., 101:852–861), and the 3' noncoding regions of the three mRNAs share 72% homology. The kα1 and Mα2 isotypes differ from the Tα1, bα1, and Mα1 isotypes by virtue of a single amino acid difference (serine to glycine) at residue 232. On the basis of these sequence similarities, it was previously speculated that Tα1 and T26 mRNAs encode functionally equivalent proteins, and that the Tα1 gene itself is specialized to produce a large pool of α-tubulin monomers when this is in high demand for neurite extension In the International Patent Application No. WO/9307280, there is disclosed a human astrocyte-specific gene expression system capable of regulating astrocyte-specific transcription of the human gene for glial fibrillary acidic protein (GFAP). This gene expression system can be used to express gene products de novo or to increase their expression in astrocytes and transgenic animals. This gene expression system can also be used to create transgenic animal models for evaluating Alzheimer's diseases.

It would be highly desirable to be provided with an isolated endogenous neuron promoter expressed during growth of both developing and mature neurons.

It would be highly desirable to be provided with a fusion gene of such a promoter linked to a marker gene wherein such a fusion gene would induce abundant expression of the marker during neurogenesis and neuronal differentiation.

It would be highly desirable to be provided with a screening assay for pharmaceutical agents that promote neuronal survival.

It would be highly desirable to be provided with a neuron promoter for targeting gene therapy to injured neurons.

It would be highly desirable to be provided with transgenic neurons expressing a neuronal promoter for use in transplantation studies.

It would be highly desirable to be provided with an in vivo model for toxicology studies.

SUMMARY OF THE INVENTION

One aim of the present invention is to provide an isolated endogenous neuron promoter expressed during growth of both developing and mature neurons.

Another aim of the present invention is to provide a fusion gene of such a neuronal promoter linked to a marker gene wherein such a fusion gene would induce abundant expression of the marker during neurogenesis.

Another aim of the present invention is to provide a screening assay for pharmaceutical agents that promote neuronal survival.

A further aim of the present invention is to provide a neuron promoter for targeting gene therapy to injured neurons.

A further aim of the present invention is to provide an in vivo model for toxicology studies.

In accordance with the present invention there is provided a DNA expression vector comprising a Tα1 α-tubulin promoter operatively linked upstream to a marker gene sequence relative to the direction of transcription in a eukaryotic expression vector adapted to be introduced into a mammal, or ancestor of said mammal at an embryonic stage and said promoter is controlling transcription of said marker gene.

The marker gene in accordance with the present invention may be selected from the group consisting of β-gal, its engineered variants, chloramphenicol-acetyl transferase and luciferase marker genes.

In accordance with the present invention the vector may be used for screening agents that promote neurogenesis or neuronal differentiation, therein said promoter is inducible during neuron growth or neuron damage and induces expression of said marker gene, thereby assaying neurogenesis or neuronal growth using said expressed marker gene.

In accordance with the present invention there is provided a transgenic non-human mammal all of whose germ cells and somatic cells contain a recombinant gene construct comprising a Tα1 α-tubulin promoter operatively linked upstream of a marker gene sequence, wherein said recombinant gene is introduced into said mammal, or ancestor of said mammal at an embryonic stage and said promoter is controlling transcription of said marker gene. Such recombinant gene construct may be integrated into a chromosome of said mammal and the promoter is inducible during neuron growth or neuron damage.

In accordance with the present invention there is further provided a method for testing material suspected of promoting neurogenesis or neuronal growth which comprises exposing a transgenic mammal of the present invention to said material and detecting said expressed marker gene as an indication of neurogenesis or neuronal growth.

In accordance with the present invention there is further provided a method of treatment of neuron damage which comprises using a DNA expression vector comprising a Tα1 α-tubulin promoter operatively linked upstream to a gene sequence relative to the direction of transcription in a eukaryotic expression vector adapted to be introduced into a mammal, or ancestor of said mammal at an embryonic stage, said promoter is targetting and controlling transcription of said gene at the desired site to treat said neuron damage.

BRIEF DESCRIPTION OF THE DRAWINGS

FIG. 1 shows the nucleotide sequence of the Tα1 α-tubulin gene 5' flanking region used in the Tα1:nlacZ transgenic mice in accordance with one embodiment of the present invention (SEQ ID NO:1);

FIGS. 2A–F shows the β-galactosidase reporter gene expression in E13.5 day embryos from 3 different lines of Tα1:nlacZ transgenic mice stained with X-gal and photographed;

FIGS. 4A–F illustrate the detection of β-galactosidase positive nuclei in sections of E13.5 embryos derived from line Q54;

FIG. 7 is the expression of the Tα1:nlacZ transgene in the adult brains of animals from line K6 (A–C) and line Q54 (D), as detected by X-gal staining.

DETAILED DESCRIPTION OF THE INVENTION

Figure 3:
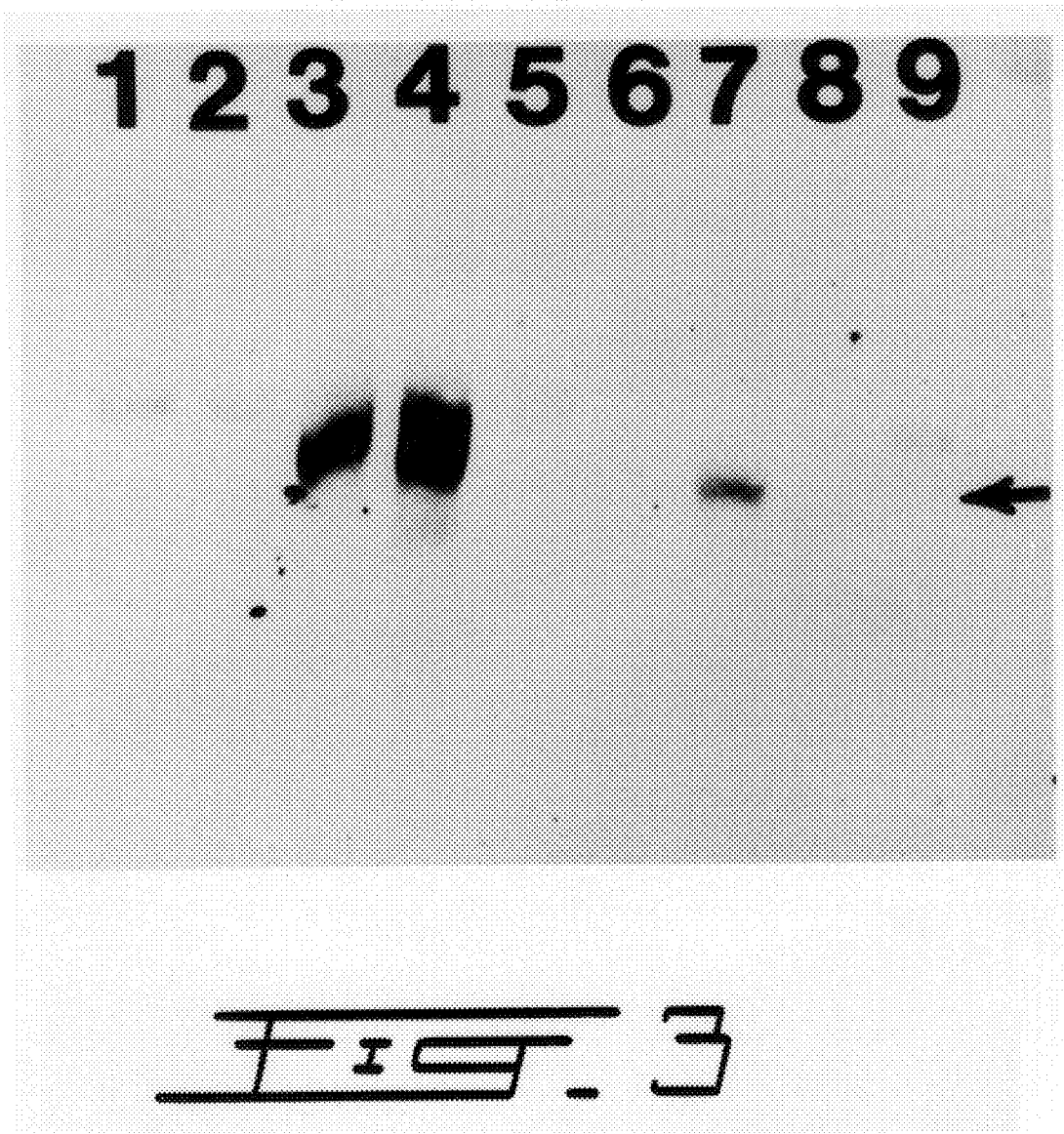
FIG. 3 is a Western blot analysis of β-galactosidase protein in equal amounts of total protein isolated from (1) control adult CD1 liver, (2) line K6 adult liver, (3) line K6 adult neocortex, (4) line K6 P1 neocortex, (5) line Q54 adult liver, (6) line Q54 adult neocortex, (7) line Q54 P1 neocortex, (8) control adult CD1 kidney, and (9) line Q54 adult kidney.

In order to define the molecular genetic mechanisms responsible for coupling expression of the Tα1 α-tubulin gene to neuronal growth, the putative promoter region of this gene was isolated, characterized, and has been fused to a nuclear β-galactosidase fusion gene to generate transgenic mice. The data of the present invention demonstrate that 1.1 kb of 5' flanking sequence from the Tα1 gene is sufficient to initiate gene expression concomitant with commitment to a neuronal fate, and to subsequently regulate gene expression as a function of morphological growth.

Surprisingly and in accordance with the present invention, it is demonstrated that neurons cultured from the transgenic mice retain expression of the transgene. The use of such transgene-positive neurons in screening assays for agents that promote neuronal survival is potentially extremely important. The expression of the marker gene in cultured embryonic neurons may be used as a rapid screen for the ability of neurotrophin peptide mimetics to support neuronal survival. The advantages of this particular promoter over other neuron-specific promoters with regards to this technology are: i) the transgene is expressed in virtually all populations of embryonic neurons, making it possible to adapt the assay to any type of neuron, ii) the transgene is highly-enriched in neurons, making glial contamination of cultures used for such screening assays unimportant, iii) the transgene is expressed virtually as soon as neurons are born, and remains expressed in adult neurons, although levels are lower, making it possible to assay neurons at any developmental stage, and iv) transgene expression is abundant, making it feasible to carry out the assays with relatively low numbers of neurons. Mice transgenic for fusion genes consisting of this promoter plus appropriate marker genes would be useful for drug screening assays.

Since, this promoter drives gene expression in injured, mature neurons, it will provide an invaluable agent for targeting genes to injured neurons via viral vectors. No other previously-characterized promoters preferentially target to injured neurons. Furthermore, the small size of this particular promoter (1 kb) greatly facilitates its use in a variety of viral vectors.

As stated, neurons cultured from this transgenic mouse continue to express the transgene. On the basis of this observation, neurons derived from such mice would prove ideal for transplantation studies. Furthermore, this promoter, could be used to drive, expression of marker genes or biologically-active molecules like trophic factors, introduced into cultured neurons, and subsequently utilized for transplantation studies. Current transplantation studies rely upon the use of retroviral promoters, which usually only drive gene expression for a short period of time following transplantation.

This promoter is expressed in injured neurons of the mature CNS, then the transgenic mice in accordance with the present invention may potentially be used to develop an in vivo model for toxicology studies. For example, if pharmacological agents lead to neuronal damage, then the expression of this marker gene would be induced, and easily assayed. No such neuronal marker for neural damage currently exists, although an astrocytic marker (GFAP expression) does.

In general, the invention features a transgenic non-human eukaryotic animal (preferably a rodent such as a mouse) whose germ cells and somatic cells contain a fusion gene construct of Tα1 α-tubulin promoter and a marker gene sequence introduced into the animal, or an ancestor of the animal, at an embryonic stage (preferably the one-cell, or fertilized oocyte, stage, and generally not later than about the 8-cell stage). A marker gene sequence, as the term is used herein, means gene which fused to the Tα1 α-tubulin promoter when incorporated into the genome of the animal, will allow assay of the induced promoter in the animal. There are several means by which such a fusion gene can be introduced into an animal embryo so as to be chromosomally incorporated in an activated state. One method is to transfect the embryo with the gene as it occurs naturally, and select transgenic animals in which the gene has integrated into the chromosome at a locus which results in activation. One such method is to transfect the embryo using a vector containing an already translocated fusion gene.

In a preferred embodiment, the chromosome of the transgenic animal includes a coding sequence (β-galactosidase), and transcription of the β-gal gene sequence is under the control of the Tα1 α-tubulin promoter sequence which is induced during neuron damage.

Library Screening

A Wistar rat lambda-DASH genomic library purchased from Stratagene was plated on a lawn of *E. coli* strain LE392. Plaque lifts were made onto nitrocellulose filters, which were probed with the end-labeled oligomers 5'-GGCAGGTTCTCTTACATCGA, and 5'-CTCTGGGCAGACGGAGGGGT, which were derived from the 5' untranslated region and the immediately 5' upstream flanking region of the previously published sequence of the Tα1 α-tubulin gene (Lemischka and Sharp, 1982, *Nature*, 300:300–355). Two identical lambda clones were identified.

Construction of the pTα1:nlacZ Transgene and Transgenic Mice

A 1.9 kb Pst I fragment containing 1.6 kb of 5' genomic flanking sequences, the region corresponding to the 5' untranslated sequences, the translation start-site (exon 1), and 200 nucleotides of intervening sequences (intron 2) was subcloned into the Pst I site of pGEM-4Z. An Sst I/Nco I partial digestion product that contained 1028 nucleotides of 5' flanking sequence, the 5' untranslated region (99 nucleotides) and the ATG translation start-site was isolated. The plasmid pMaori3 was cut with Sst I and Nco I (which cuts at the translation start-site of the nlacz gene in this plasmid), and ligated in the Tα1 Sst I/Nco I fragment, thereby replacing the CMV promoter with the Tα1 5' flanking region. pMaori3, which is a derivative of pnlacF was kindly provided by Dr. Eric Mercer (Mercer et al., 1991, *Neuron*, 7:703–716). This plasmid contains a CMV promoter linked to a lacZ gene that has had a nuclear translocation signal inserted in frame with the lacZ coding sequence to encode a nuclear-targeted version of *E. coli* β-galactosidase. pMaori3 also includes, downstream to the lacZ gene, the murine protamine-1 gene from +95 relative to the transcription start site to +625, which provides an intron and a poly(A) adenylation signal and site. The Tα1:nlacZ transgene was then excised from this plasmid using Sal I and Eco RI, and subcloned into the same two sites in the pUC19 polylinker. The transgene fragment was isolated free of vector sequences from this plasmid by digestion with Hind III and Xba I. Sequencing of the Tα1 promoter fragment was performed to obtain completely overlapping sequence information in both directions.

Transgenic mice were generated by the Networks of Centers of Excellence for Neural Regeneration and Recovery transgenic core facility. Presence of the transgene was identified by tail blots. Animals from 8 Tα1-nlacZ lines were identified, 5 of which showed expression.

lacZ Staining Technique

Embryos and brains were prepared for *E. coli* β-galactosidase staining by fixing for 60 minutes at 4° C. in fresh 4% paraformaldehyde, 0.1 M $NaH_2PO_4$ (pH 7.3). They were then rinsed three times, for 30 minutes each, with a wash containing 0.1 M $NaH_2PO_4$ (pH 7.3), 2 mM $MgCl_2$, 0.1% sodium deoxycholate, and 0.02% NP-40. The staining reaction was performed by incubating the tissue for 16–24 hours at 37° C. in a reaction mix containing all the components of the rinse buffer with the addition of 1 mg/ml X-Gal, 5 mM $K_3Fe(CN)6$, and 5 mM $K_4Fe(CN)_6$ (at pH 7.3–7.6). A postfixation was performed for 24–48 hours in 4% paraformaldehyde. Embryos to be used for sectioning were cryoprotected in graded sucrose solutions, as previously described by Miller et al. (1987, *J. Cell. Biol.*, 105:3065–3073), and sectioned on the cryostat.

Western Blot Analysis

Frozen tissues were crushed and homogenized in lysis buffer (20 mM Tris, 1% Triton X™, 5 mM EDTA, 100 mM PMSF, 1:1000 leupeptin, 1:1000 aprotinin) by passing the homogenate through a 22 gauge needle. Protein concentrations were determined using a bicinchoninic acid protein assay (Sigma). Proteins were separated on an, 8% SDS polyactylamide gel. The gel was rinsed in Towbin™ buffer, and the proteins transferred to nitrocellulose using a Hoefer™ semi-dry transfer unit. The nitrocellulose was blocked for one hour with 5% dried milk in PBS with 0.3% Tween™, washed three times in PBS with 0.1% Tween™, and incubated with 1:5000 rabbit anti-β-galactosidase for 1 hour (Cappel, Durham, N.C.). The filters were subsequently washed three times with PBS plus 0.1% Tween™, and incubated with a 1:5000 dilution of peroxidase-conjugated goat anti-rabbit antibody for 1 hour (Jackson Labs). The ECL system was used to visualize reactive proteins (Amersham).

In Situ Hybridization

In situ hybridization on E16 rat embryos was performed as previously described by Miller et al. (1987, *J. Cell. Biol.*, 105:3065–3073). Briefly, embryos were isolated, immersion fixed in 4% paraformaldehyde overnight, cryoprotected through graded sucrose solutions (12%, 16% and 18%), frozen, and sectioned onto chrom-alum subbed slides. Anti-sense 35S RNA probes specific for Tα1 α-tubulin mRNA were generated and hybridized to these sections as described by Miller et al. (1989, *J. Neurosci.*, 9:1452–1463). Slides were then dipped in Kodak™ NTB-3 emulsion, exposed for 5–10 days, developed, and analyzed using darkfield microscopy.

Primary Neuronal Cultures

Whole brains from E14 Tα1 α-tubulin CD1 transgenic mice, bred and maintained by the transgenic facility at the University of Alberta, were mechanically dissociated with a fire-polished Pasteur™ pipette in serum-free medium composed of 1:1 mixture of Dulbecco's modified Eagle's medium (DMEM) and F-12 nutrient (GIBCO), including glucose (0.6%), glutamine (2 mM), sodium bicarbonate (3 mM), HEPES buffer (5 mM) [all from Sigma except glutamine (GIBCO)] and a defined hormone mixture. Cells ($0.5 \times 10^6$/ml) were plated on poly-L-ornithine-coated (15 ug/ml; Sigma) glass cover-slips in 24 well Nunclon™ (1.0 ml/well) culture dishes.

Antibodies

Rabbit anti-human β-galactosidase serum (β-gal; used at 1:500 for immunocytochemistry and 1:5000 for Western blot analysis) was purchased from Cappel. Alternatively, a mouse monoclonal anti-β-galactosidase serum (obtained from the Hybridoma Core Facility of the NCE for Neuronal Regeneration and Recovery) was used for some studies. Rabbit anti-human neuron-specific enolase serum (NSE; used at 1:2000) was purchased from Polysciences. Mouse monoclonal antibody to human glial fibrillary acidic protein (GFAP; used at 1:100) was purchased from Boehringer Mannheim. Rabbit antiserum to human galactocerebroside (GC; used at 1:200) was purchased from Chemicon. Fluorescein- or rhodamine-conjugated affinipure goat antibodies to mouse or rabbit IgGs were obtained from Jackson.

Immunocytochemistry and Quantification

Indirect immunocytochemistry was carried out on cells that were cultured for 1,2,3,6 and 8 days in vitro (DIV) on glass coverslips. All coverslips were fixed with 4% paraformaldehyde for 30 minutes followed by three (10 min. each) washes in phosphate buffered saline (PBS). The cells were then permeabilized with 0.1% Triton-X™ in PBS for 5 minutes followed by three (10 min each) washes in PBS. For dual labeling experiments the primary antibodies were added together. Following the PBS rinse the coverslips were incubated in the primary antibodies in PBS/10% normal goal serum for 2 hours at 37° C. Coverslips were rinsed three times (10 min each) in PBS and incubated in secondary antibodies (1:100 for fluorescein-conjugated antibodies and 1:200 for rhodamine-conjugated antibodies) in PBS for 30 minutes at 37° C. Coverslips were then washed three times (10 min each) in PBS, then rinsed in water, placed on glass slides and coverslipped with Fluorsave™ as the mounting medium. Fluorescence was detected and photographed with a Zeiss™ photomicroscope.

To determine the percentage of cells that were dual labeled with Ogalactosidase and NSE, GFAP or GC, the cells that were immunopositive for β-gal were counted first, then the fluorescent filter was changed to count the cells within that population that were positive for a phenotype marker. The count was random across 4–5 fields on each coverslip and carried out with a Zeiss™ photomicroscope. In each experiment, at least three coverslips were examined, and this was done in three independent culture experiments.

Sequence of the Tα1 α-Tubulin Gene 5' Flanking Region

The transcription start-site of the Tα1 gene, and the DNA sequences immediately 5' to the start-site have previously been characterized. To isolate a genomic clone containing further 5' flanking sequences, oligonucleotides homologous to the 5' untranslated region of the mRNA and to the region immediately 5' to the start-site were used to screen a rat genomic library. Two identical lambda clones were identified, and a 1.9 kb Pst I fragment was subcloned into pGEM-4Z. This insert contained 1.6 kb of 5' genomic flanking sequences, the region corresponding to the 5' untranslated . sequence in the mRNA as well as the translation start-site (exon 1), followed by 200 nucleotides of intervening sequences (intron 1). This subclone was used to generate an Sst I/Nco I partial digestion product that contained 1028 nucleotides of 5' flanking sequence, the entire 5' untranslated region (99 nucleotides), and the ATG translational start-site. This fragment was used to construct a Tα1:nlacZ fusion gene for generation of transgenic mice.

The sequence of the 5' flanking region contained in the fusion gene is shown in FIG. 1. This gene has a consensus TATAA box commencing at −30 relative to the transcription start-site. Immediately upstream of the TATAA box are a retinoic acid receptor half-site (one of four such elements in this DNA fragment) at −41 and a consensus AP2 site (one of 5 such elements) at −54. Fifteen nucleotides further upstream at −69 is a consensus PEA-3 site which is induced, like AP2, in response to TPA, growth factors, and serum, and which appears to be a primary signal transduction target. Thus, within the first 70 nucleotides of the transcription start-site of this gene, there are 3 consensus binding sites for factors that mediate cellular responses to extrinsic cues.

Somewhat further upstream, at −143, is a consensus sequence binding element for the CCAAT-enhancer binding protein which, although it has been best-characterized in other tissues, is expressed in brain. At −214 is another one of the 5 consensus AP-2 sites, with two additional AP-2 sites in close proximity at −260, and −291. These latter two AP-2 sites bracket a region of the Tα1 promoter that shows high homology to the human bα1 α-tubulin 5' flanking sequences; of 330 upstream nucleotides from this latter gene that have been characterized, this is the only region of homology. Moreover, embedded within this 19 nucleotide region of homology between the human and rat genes is a sequence that has been found at approximately the same location in both the peripherin and the VGF genes. A second, similar element is located at −902. These genes share in common with the Tα1 gene their nervous system-specific expression and, in the case of peripherin, a similar developmental profile. Moreover, both of these genes, like the Tα1 gene, are upregulated by NGF in PC12 cells. The next 200 nucleotides of this promoter are relatively devoid of recognizable sequence motifs with the exception of two gamma-interferon response elements at −392 and −468. One additional gamma-interferon response element is located at −664. Although the gamma-interferon response element is relatively loose in terms of its consensus sequence, these motifs are notable because the Tα1 α-tubulin gene is induced following injury to either peripheral (Miller et al., 1989, *J. Neurosci.*, 9:1452–1463) or central (Tetzlaff et al., 1992, *J. Neurosci.*, 11:2528–2544) neurons. In this regard, an NF-IL6 consensus element, which also mediates inflammatory responses, is located in the Tα1 promoter at −899.

From −680 to −490 is a region of the promoter that contains a number of sequence elements that are interesting from a developmental perspective. Firstly, this region contains 3 consensus retinoic acid receptor half-sites at −496, −618, and −669. One of these comprises part of an imperfect estrogen-response element at −676 to −662 (one of two, with the other being located at −959). Secondly, this region contains two consensus E-box binding sites for members of the basic helix-loop-helix (bHLH) family at −530 and −633. Thirdly, between these two E-box elements are two tandem consensus elements from −571 to −541 for the Drosophila homeodomain proteins antennapedia, ultrabithorax, and fushi tarazu.

The endogenous Tα1 α-tubulin gene is expressed at high levels in developing neurons during morphological growth, is down-regulated following neuronal maturation, and is then expressed in mature neurons as a function of extrinsic cues that regulate growth. In accordance with the present invention, it is demonstrated that 1.1 kb of 5′ flanking region from the Tα1 gene is sufficient to specify a similar pattern of gene expression in transgenic mice. More specifically, the Tα1:nlacZ transgene described here is induced concomitant with commitment to a neuronal fate, and is then regulated as a function of neuronal growth. Thus, this promoter fragment is sufficient to regulate gene expression in a cell type-specific, developmentally-appropriate fashion.

The data presented in accordance with the present invention indicate that the Tα1:nlacZ transgene is induced. early relative to neuronal commitment. Although it is difficult to establish a relationship between transgene expression and the birth of neurons in the developing brain using the approaches described here, such a relationship can be addressed in the developing peripheral nervous system. In this regard, the present data suggest that, at least for developing sympathoblasts, the Tα1:nlacZ transgene is expressed prior to terminal mitosis. This conclusion is based upon the fact that numerous β-galactosidase-positive cells were detected in the superior cervical ganglion at E11.5, a timepoint when sympathetic neurons are just starting to be born. Furthermore, at E10.5, when the ganglion itself is not yet anatomically distinct, transgene-expressing cells were detected in the appropriate region adjacent to the dorsal aorta.

In agreement with these observations, the pattern of transgene expression in the developing dorsal root ganglia and retina also indicated that induction occurred either prior to, or coincident with, terminal mitosis. Sensory neurons of the dorsal root ganglia are born commencing around day 10.5 in the mouse, with the time of peak genesis being E11.5–E12.5. In the Tα1:nlacZ transgenic mice, β-galactosidase positive nuclei were detected in the developing ganglia as soon as they were anatomically discrete: the first positive cells were detected at E10.5 in ganglia that were coalescing at mid-spinal cord level, with intense β-galactosidase staining being detected in the full cohort of dorsal root ganglia by E11.5. In the embryonic retina, it was possible to establish an even more precise correlation between mitosis and transgene induction. Progenitor cells of the E13.5 mouse retina undergo neurogenesis in the neuroblast layer, and subsequently migrate to the ventricular zone to undergo mitosis. Some of these cells migrate back to the neuroblast layer, only to return to the ventricular zone for subsequent mitoses. Others commit to a retinal ganglion cell or amacrine cell fate, and migrate through the neuroblast layer to the retinal ganglion cell layer or to the immediately adjacent region. Surprisingly, we observed transgene-positive cells not only in the retinal ganglion cell and neuroblast layers, but also in the ventricular zone. Thus, either the Tα1:nlacZ transgene is induced in neuroblasts prior to terminal mitosis, or it is induced as soon as neurons have undergone terminal mitosis.

The in vitro observations of the present invention are consistent with this conclusion. In primary mixed-cultures derived from the E14 brain, two populations of β-galactosidase positive cells were detected. One population, which comprised approximately 50% of the total, expressed both β-galactosidase and neuron-specific enolase, and presumably represented postmitotic neurons. The second population of β-galactosidase positive cells, which comprised the other 50%, expressed none of the cell type-specific markers that were used in this study. In light of the in vivo data, it is suggested that these cells represent either neurons that are just postmitotic, or neuroblasts that are still dividing. Either alternative is consistent with the conclusion that the Tα1 promoter specifies gene expression coincident with the neuronal commitment decision.

The studies presented here also indicate that, subsequent to it's initial induction, the Tα1:nlacZ transgene is regulated as a function of neuronal growth and morphology. Three observations support this conclusion. Firstly, at E13.5, the transgene is expressed at the highest levels in those neuronal populations that are undergoing extensive axogenesis, such as spinal cord motor neurons and retinal ganglion cells. Secondly, transgene expression is downregulated in the developing brain as a function of neuronal maturation. Finally, expression of the transgene in the mature nervous system is highest in large projection neurons and/or in those neurons that remain capable of significant growth and remodeling. Thus, the Tα1 α-tubulin promoter does not simply encode neuronal-specificity, but somehow targets high levels of gene expression to those neurons that are elaborating or maintaining an extensive axonal or dendritic arbor.

Such specification could be a function of intrinsic and/or extrinsic mechanisms. Thus, the Tα1 α-tubulin gene might be induced to low basal levels in all neurons, but, inasmuch as neuronal morphology is an inherent neuronal characteristic, increased levels of Tα1 gene expression might be determined as a function of whether a given neuron will be, for example, a projection neuron versus an interneuron. Alternatively, the Tα1 α-tubulin promoter might target basal levels of gene expression to all neurons, with absolute levels of expression being entirely dependent upon the presence or absence of appropriate environmental cues. Previous studies demonstrating that this gene is regulated as a function of NGF exposure in responsive neurons (Mathew and Miller, 1990, *Dev. Biol.*, 141:84–92; Miller et al., 1991; Ma et al,. 1992, *J. Cell. Biol.*, 117:135–141), is consistent with this latter explanation. However, perhaps the most plausible explanation invokes both of these mechanisms: levels of Tα1 gene expression may be partially determined as a function of the morphological phenotype of any given neuron, but the absolute levels of expression are likely regulated as a function of extrinsic cues like growth factors.

Together, these studies indicate that 1.1 kb of 5′ flanking sequences from the Tα1 α-tubulin gene are sufficient a) to specify gene expression as a function of commitment to a neuronal phenotype, and b) to regulate levels of gene expression as a function of morphological growth. Although the sequence elements responsible for this pattern of gene expression are undefined, sequence analysis of the promoter region utilized in this transgene revealed the presence of a number of intriguing motifs. Firstly, this promoter region contains a large number of sequence elements that mediate responses to extrinsic cues. More specifically, this promoter fragment contains five (5) AP-two (2) sites, a PEA-3 site, two (2) imperfect estrogen response elements, an NF-IL6 binding site, and three (3) gamma-interferon response elements. The AP-2 and PEA-3 sites are both believed to be primary targets of signal transduction events, and to mediate nuclear responses to a variety of extrinsic cues ranging from retinoic acid to growth factors. These elements could therefore play an important role in regulating the Tα1 gene in response to ongoing environmental cues. The NF-IL6 binding site and gamma-interferon response elements may be equally important: Tα1 α-tubulin mRNA levels increase following neuronal injury (Miller et al., 1989, *J. Neurosci.*, 9:1452–1463), and at least a subset of injury-induced alterations in mature peripheral neurons are due to inflammatory responses. In addition to sequence elements that mediate responses to the environment, the Tα1 promoter fragment includes two other clusters of sequence motifs that are particularly interesting. One cluster is located at −295 and includes, within 45 nucleotides, two AP-2 sites, and a 19 nucleotide region of homology with the promoter of the human bα1 α-tubulin gene. With regards to the latter, this represents the only significant region of homology between the 5' flanking regions of the rat and human genes in the approximately 330 nucleotides that have been characterized from the human. Moreover, this region bears high homology to a previously-noted sequence element found in a similar position in the 5' flanking regions of the peripherin and VGF genes. Interestingly, although the peripherin gene is not expressed in all neurons, as is the Tα1 gene, it is expressed in a subpopulation of developing neurons early in embryogenesis, is downregulated as a function of neuronal maturation, and is subsequently reinduced during neuronal regeneration.

The second cluster of consensus elements occurs from −670 to −490 and includes 3 retinoic acid half-sites, one of which overlaps with an estrogen response element, 2 E-box motifs (consensus elements for members of the bHLH transcription factors), and 2 tandem consensus sequence elements for a number of Drosophila homeodomain proteins. Each one of these three different classes of transcription factors have been implicated during development of the mammalian nervous system. For example, elevated levels of retinoic acid during embryogenesis perturb both amphibian and mouse neural development. Furthermore, retinoic acid promotes survival and neurite outgrowth from primary cultured neurons.

Basis helix-loop-helix (bHLH) transcription factors have also been implicated in neural commitment decisions. In Drosophila, commitment to, a neuronal phenotype involves the interplay between positive and negative intracellular mediators, many of which are members of this family of transcription factors. bHLH proteins encoded by the achaete-scute locus are positive factors that are essential for commitment to a neuronal phenotype, while bHLH proteins of the "Enhancer of split" complex are inhibitory. Mammalian homologues of both achaete-scute and "Enhancer of split" have been identified and are expressed in a fashion that is consistent with a role in neuronal commitment decisions.

Finally, the precise functions of the mammalian homeodomain proteins are still not defined, but it is clear that at least some of these proteins play an essential role during mouse neural development, as demonstrated by either overexpressing or mutating these genes in transgenic mice. As stated, the Tα1 α-tubulin promoter contains two tandem consensus sequence elements for antennapedia, ultrabithorax, and fushi tarazu. The homologous proteins in mouse are encoded by multigene families that are expressed throughout the developing nervous system, with each individual member being expressed in a spatially-restricted fashion. Despite the obvious functional importance of these transcription factors, their downstream targets remain elusive. It is possible, based on the structural and functional similarities between the Drosophila and mammalian proteins, that a subset of mammalian homeodomain proteins may bind to these motifs and thereby play a role in determining the developmental pattern of Tα1 α-tubulin gene expression.

In summary, the Tα1 α-tubulin promoter described here is sufficient to specify gene expression coincident with commitment to a neuronal fate and to regulate levels of gene expression as a function of neuronal growth.

The present invention will be more readily understood by referring to the following examples which are given to illustrate the invention rather than to limit its scope.

EXAMPLE I

Tα1:nlacZ TRANSGENE EXPRESSION IN THE EMBRYONIC NERVOUS SYSTEM

To determine whether 1.1 kb of 5' flanking sequences from the Tα1 α-tubulin gene was sufficient to direct gene expression to developing neurons, a Tα1:nlacZ fusion gene was made and tested in transgenic mice. The 1127 nucleotide Sst I-Nco I partial digest fragment was fused to an Nco I site located at the ATG translation start-site of a modified *E. coli* lacZ gene derived from pMaori 3. This lacZ gene contains an SV40T antigen nuclear localization signal inserted in front of the lacZ gene, and has previously been used in transgenic mice (Mercer et al., 1991, *Neuron*, 7:703–716). A DNA fragment containing the Tα1:nlacZ construct free of vector sequences was isolated and injected into fertilized mouse eggs to generate transgenic founder animals. Transgenic animals were assayed for nlacZ expression by incubating tissues in a staining solution containing X-Gal, a reagent that leads to deposition of blue crystals in cells with an active *E. coli* β-galactosidase.

A total of 8 lines bearing Tα1:nlacZ transgenes were examined For all founder lines, embryonic day 13.5 (E13.5) embryos were assessed by histochemical staining with X-gal. At this developmental stage, expression of the endogenous Tα1 gene is highly abundant in the embryonic nervous system. Bacterial β-galactosidase activity was detected in embryos derived from 5 of these lines. Levels of expression of the transgene in these 5 lines did not correlate with transgene copy number.

In all 5 positive lines, expression of the transgene was detected only within the developing nervous system (FIG. 2), consistent with the nervous system-specific expression of the endogenous gene. In four of the five, lines Q54, K6, O12, and Q27, expression of the transgene at E13.5 was detected throughout the developing central nervous system, including the brain, spinal cord, and retina, and, within the peripheral nervous system, in sympathetic, parasympathetic, and sensory ganglia (FIGS. 2A–D). In the fifth line, line Tα1Zl, expression of the transgene at E13 was detected only in a subset of these sites, including the retina, dorsal root ganglia, and the developing mesencephalon; these sites appeared to be those with the highest levels of staining in the other lines.

Two of the lines, Q54 and K6, were chosen for more extensive analysis. The pattern of expression of the Tα1:nlacZ transgene was similar in embryos derived from both lines, although the K6 line expressed higher levels of the transgene, as indicated by the rapidity and intensity of staining with X-gal (FIGS. 2A and 2C). This difference was confirmed by Western blot analysis of the neonatal cortex, which revealed that line K6 expressed much higher levels of β-galactosidase than did line Q54 (FIG. 3).

To precisely determine the location of the cells expressing the transgene, E13.5 embryos from both lines were stained with X-gal and sectioned. For line Q54, nuclei positive for β-galactosidase were distributed throughout the embryonic nervous system (FIGS. 2C and 4). β-galactosidase positive cells were detected in the sensory ganglia, including the developing cranial ganglia (FIG. 4A) and all of the dorsal root ganglia (FIGS. 2C and 4D). Positive cells were distributed throughout the developing autonomic nervous system, in both sympathetic ganglia (FIG. 4B) and parasympathetic neurons of, for example, the gut (FIG. 4C). Within the central nervous system, transgene-positive nuclei were detected in the retina, and throughout the spinal cord, myelencephalon, metencephalon, diencephalon, and the developing olfactory lobes (FIGS. 2C, 4E and 4F). At this age, some positive nuclei were detected in the developing neocortex, but one day later, at E14.5, numerous positive cells were detected in the cortical plate region (FIG. 2D).

In line K6, where transgene expression is many times higher than in Q54, β-galactosidase staining was detected throughout the E13.5 nervous system in a pattern that appeared to be panneuronal (FIG. 2A). However, at this developmental stage, the β-galactosidase gene product was not limited to nuclei, presumably because of the very high levels of expression, making mapping of positive cells less definitive than in line Q54.

Figure 5A:
FIG. 5 is a comparison of the distribution of the endogenous Tα1 α-tubulin mRNA in the developing rat embryo at E16 (A,B) versus the Tα1:nlacZ transgene in line Q54 transgenic mice at E13.5 (C,D)
Figure 5B:
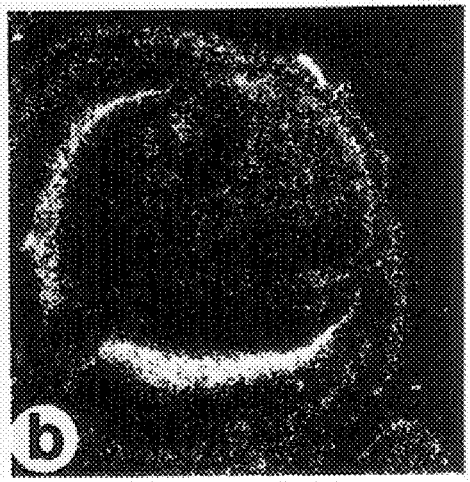
Figure 5C:
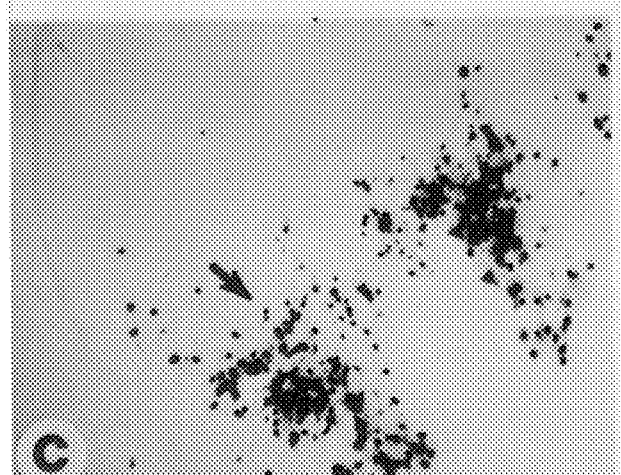
Figure 5D:
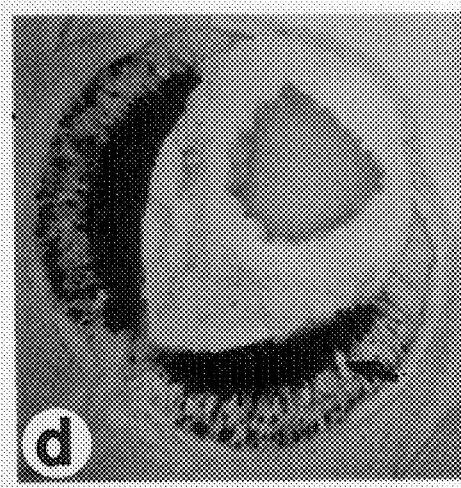

The endogenous Tα1 α-tubulin gene is expressed at the highest levels in those locations within the developing nervous system where neurons are undergoing extensive morphological growth. Expression of the transgene was similarly regulated (FIG. 5), as exemplified by its expression in the developing spinal cord and retina. In the spinal cord, at E16, the endogenous Tα1 mRNA is expressed at the highest levels in the ventral horn, which contains motor neurons that are under-going axogenesis, with significantly lower levels in the dorsal horn (FIG. 5A). The Tα1:nlacZ transgene is expressed in a similar fashion in transgenic mice at E13.5: in line Q54, β-galactosidase positive nuclei were highly enriched in the developing ventral horn, with few positive cells in the dorsal horn (FIG. 5C). A similar correlation between expression of the endogenous gene and the transgene was noted in the developing retina. At E16 in the rat, many retinal ganglion cells have been born, have migrated, and are extending their axons to form the nascent optic nerve. At this developmental stage, the endogenous Tα1 gene is expressed at high levels within the retina and, more specifically, within the retinal ganglion cell layer, as detected using in situ hybridization (FIG. 5B). At E13.5 in the mouse, the transgene is also expressed at the highest levels in the retinal ganglion cell layer (FIG. 5D). Interestingly, A-galactosidase-positive nuclei were also noted in the ventricular zone of the developing retina, where retinal precursor cells are dividing, and in the neuroblast layer, where neurogenesis is occurring, and through which the newly-committed retinal ganglion cells migrate prior to undergoing differentiation and axogenesis in the retinal ganglion cell layer. These transgene-positive cells might represent premitotic neuroblasts that are committed to a neuronal fate, but are still undergoing division. Alternatively, they might represent newly-committed neurons prior to their migration from the ventricular zone that have induced the. transgene immediately following terminal mitosis.

To determine the time of onset of Tα1:nlacZ expression, embryos from lines K6 and Q54 were examined at earlier timepoints. In both lines, positively-staining cells were detected within the developing spinal cord and brain at the earliest timepoint examined, E9.5. By E10.5 (FIG. 2f), β-galactosidase positive cells were detected throughout the developing spinal cord and, in the brain, in the myelencephalon, metencephalon, and diencephalon. By E11.5, the level and location of β-galactosidase expression in the developing central nervous system was similar to that seen in the E13.5 embryo, with the exception that staining was not yet detected in the retina or in the developing cortical plate (FIG. 2E). The onset of transgene expression within peripheral ganglia over this time frame was coincident with, and potentially prior to, the birth of sensory and sympathetic neurons. Neuralcrest derived sensory neurons are born commencing at approximately day 10.5 in the mouse, with the time of peak genesis being E11.5–E12.5. In animals from line Q54, β-galactosidase-positive nuclei were detected in the region of the coalescing dorsal root ganglia, as soon as the first ganglia were recognizable at E10.5 (FIG. 2F). By E11.5, all of the dorsal root ganglia (which, at this stage, ranged the entire length of the spinal cord) stained intensely for β-galactosidase, as did the sensory cranial ganglia (FIG. 2E). Similar early expression of the transgene was observed in the developing sympathetic chain. In line Q54 at E10.5, many β-galactosidase positive cells were detected in the region of the dorsal aorta where the superior cervical ganglia will eventually form, but, at this developmental stage, no ganglionic organization was yet apparent. By E11.5, the superior cervical ganglia were readily distinguishable, and contained numerous β-galactosidase-positive nuclei. The time course of expression, and number of positive cells in the SCG over this developmental window was somewhat surprising, given the fact that the first post-mitotic neurons are born at around E12 in the mouse SCG, suggesting that the transgene may be induced in sympathoblasts prior to terminal mitosis.

EXAMPLE II

EXPRESSION OF THE Tα1:nlacZ TRANSGENE IN CULTURED NEURONS AND GLIAL CELLS

To determine the identity of the transgene-positive cells that were observed in vivo, primary mixed cultures derived from line K6 were analyzed immunocytochemically. More specifically, mixed cultures derived from whole brains of E14 transgenic embryos were plated onto poly-L-ornithine coated glass cover-slips, and were cultured for 1,2,3,6 and 8 days in vitro (DIV). These cultures were then double-labeled with antibodies specific for β-galactosidase, and for one of three different markers: neuron specific enolase (NSE) for neurons, glial fibrillary acidic protein (GFAP) for astrocytes, and galactocerebroside (GC) for oligodendrocytes.

To determine the identity of transgene-expressing cells in these cultures, β-galactosidase-positive cells were first identified, and then the filter was changed to determine whether these cells were positive for a second, cell type-specific marker (FIG. 6). In cultures that were double-labeled with GFAP, of 1964 β-galactosidase-positive cells that were counted (ranging from 312 to 496 cells at each of 1, 2, 3, 6, and 8 DIV), none were positive for this astrocytic marker (FIGS. 6C and D). Similarly, in cultures ranging from 1–8 DIV that were double-labeled with GC, of 576 β-galactosidase-positive cells that were counted (ranging from 90 to 183 at each timepoint), none were positive for this oligodendrocyte marker (FIGS. 6E and F). Thus, neither astrocytes nor oligodendrocytes expressed the Tα1:nlacZ transgene.

Figure 6A:
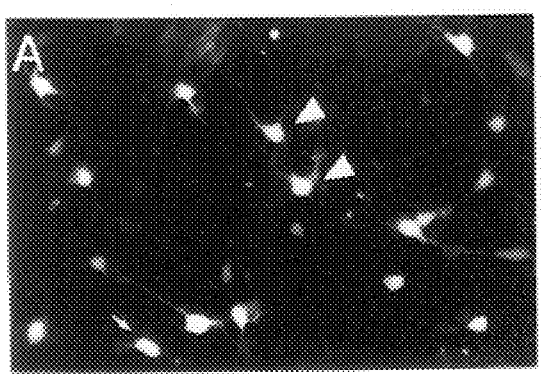
FIG. 6 is a co-localization of β-galactosidase immunoreactivity with neuronal but not glial cells in primary mixed cultures derived from transgenic E14 brains of line K6.
Figure 6B:
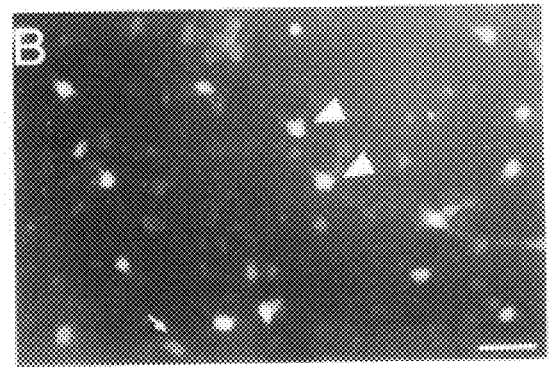
Figure 6C:
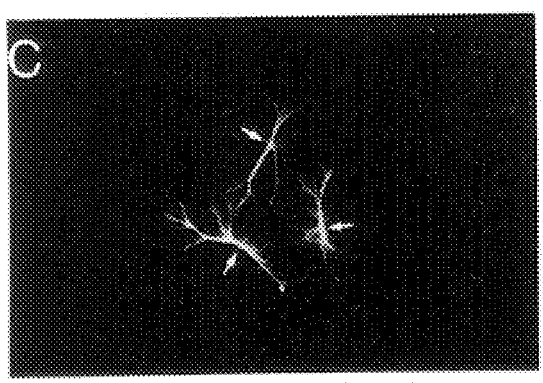
Figure 6D:
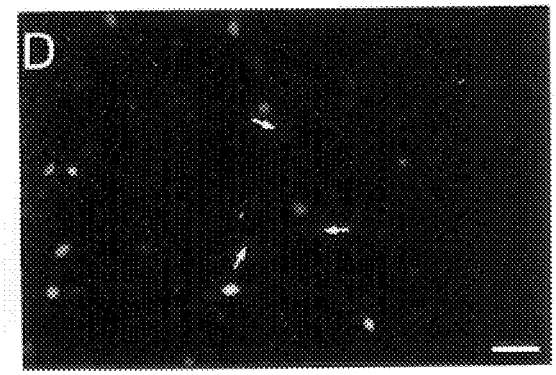
Figure 6E:
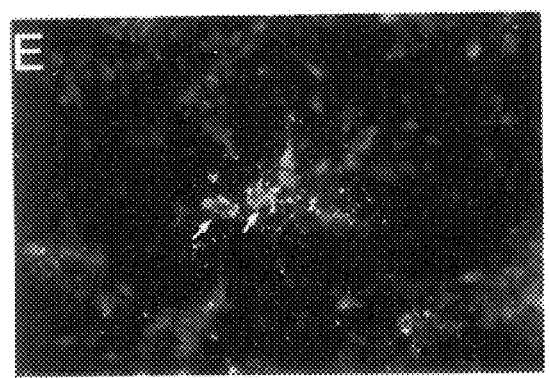
Figure 6F:
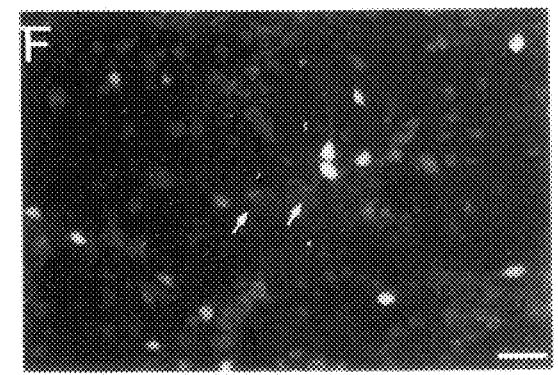

In contrast, at all timepoints from 1 to 8 DIV, a large percentage of β-galactosidase positive cells were positive for NSE (FIGS. 6A and B). At 1,2,6, and 8 DIV, of 400–600 β-galactosidase positive cells counted at each timepoint, 50–60% were NSE-positive. At 3 DIV, the percentage of β-galactosidase-positive, NSE-positive cells was somewhat lower, being approximately 35–40%. Thus, the Tα1:nlacZ transgene was expressed in neurons. The identity of the β-galactosidase positive cells that were not NSE-positive is somewhat speculative, since they were not, on the basis of the GFAP and GC double-label studies, glial cells. Instead, they may represent early postmitotic neurons that have not yet induced NSE or, in light of the in vivo data, they may represent neuroblasts that have not yet become postmitotic.

EXAMPLE III

REGULATION OF THE Tα1:nlacZ TRANSGENE DURING NEURONAL MATURATION

These developmental data indicated that the Tα1:nlacZ transgene was induced parallel with the neuronal commitment decision, and was then expressed, like the endogenous gene, at the highest levels in neuronal populations that were undergoing extensive process extension. It was previously demonstrated that Tα1 α-tubulin mRNA levels decrease coincident with neuronal maturation. To determine whether the Tα1 promoter region utilized in the transgene contained the sequences responsible for this developmental downregulation, β-galactosidase levels in the neocortex of adult was compared versus newborn Tα1:nlacZ mice from lines Q54 and K6 (FIG. 3). Western blot analysis revealed that, in both lines, transgene expression was downregulated as the neocortex matured (FIG. 3). Similar Western blot analysis of the adult liver and kidney revealed the tissue-specificity of transgene expression, with detectable β-galactosidase levels only present in the adult cortex samples (FIG. 3).

The endogenous Tα1 α-tubulin mRNA is expressed in most, if not all, mature neurons, with the highest relative levels in large projection neurons and in those neurons that remain capable of significant growth, like the locus coeruleus. To determine whether the transgene was regulated in the same fashion, adult brains from lines K6 and Q54 were stained with X-gal. For line Q54, most of the adult brain was devoid of β-galactosidase staining (FIG. 7D), confirming the Western blot results (FIG. 3). However, β-galactosidase expression was detectable in a number of neuronal populations, including, for example, the hippocampal granule and pyramidal cells, where expression of the endogenous Tα1 gene remains high in the adult. In contrast, in line K6, although β-galactosidase levels were markedly decreased from embryonic levels (FIG. 3), transgene expression was detectable in many, if not all, mature neurons (FIGS. 7A–7C). However, like the endogenous gene, expression was not uniform in all populations of neurons. For example, expression was high in the hippocampal formation, including the hippocampus proper as well as the entorhinal cortex (FIG. 7B). Moreover, in the mature cortex, the transgene was expressed in a laminar fashion, which was particularly striking in the more caudal regions. Thus, the pattern of expression of the Tα1:nlacZ transgene in the mature nervous system was similar to that observed for the endogenous gene.

Figures 8A, 8B:
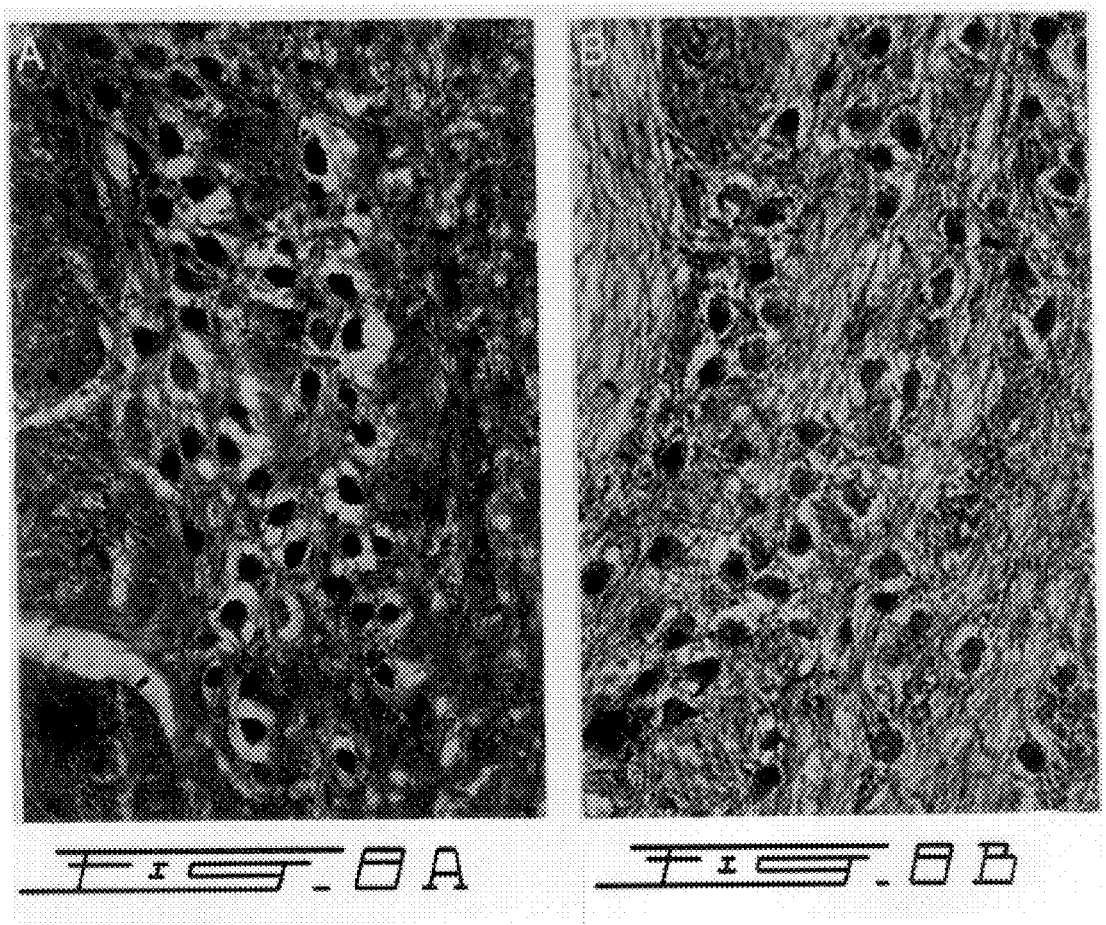
FIG. 8 illustrates the increase in transgene expression in injured, mature facial motoneurons (A) relative to uninjured neurons on the contralateral side of the same section (B), as detected by X-gal staining.

The endogenous Tα1 α-tubulin gene is upregulated in mature neurons following axonal injury. To determine whether the transgene was similarly increased, the facial motoneurons of adult transgenic mice were unilaterally crushed and, five days postinjury coronal sections through the facial nuclei were stained for β-galactosidase. This analysis demonstrated a dramatic increase in X-gal staining in axotomized motoneurons as compared to contralateral uninjured neurons (FIG. 8). Thus, this promoter contains the sequence elements responsible for increasing neuronal gene expression as a function of neuronal damage.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated nucleic acid molecule comprising a Tα1 α-tubulin promoter, wherein said promoter comprising the 5' flanking region immediately upstream of the 5' untranslated region of a gene encoding rat Tα1 α-tubulin, wherein said 5' flanking region comprises an SP-2 site, a consensus PEA-3 site, an NF-IL-6 binding site, a γ-interferon response element and a consensus sequence binding element for the CAATT-enhancer binding protein.

2. The nucleic acid molecule of claim 1, wherein said 5' flanking region comprises nucleotides 1–1028 of SEQ ID NO: 1.

3. A DNA expression vector comprising a Tα1 α-tubulin promoter, wherein said promoter comprising the 5' flanking region immediately upstream of the 5' untranslated region of a gene encoding rat Tα1 α-tubulin, wherein said 5' flanking region comprises an SP-2 site, a consensus PEA-3 site, an NF-IL-6 binding site, a γ-interferon response element and a consensus sequence binding element for the CAATT-enhancer binding protein.

4. The DNA expression vector of claim 3, wherein said 5' flanking region comprises nucleotides 1–1028 of SEQ ID NO: 1.

* * * * *

UNITED STATES PATENT AND TRADEMARK OFFICE
CERTIFICATE OF CORRECTION

PATENT NO.　　: 6,309,876 B1
DATED　　　　 : October 30, 2001
INVENTOR(S)　 : Freda Diane Miller, Andrew Gloster, Grace Causing and Jean George Toma It is certified that error appears in the above-identified patent and that said Letters Patent is hereby corrected as shown below:

<u>Title page,</u>
Item [75], Inventors, replace "Edmonton," with -- Edmonton, Alberta, Canada --;
Item [73], Assignee, replace "Montreal (CA)" with -- Montreal, Quebec, Canada --;
Item [56], References Cited, under OTHER PUBLICATIONS, within the Matthew and Miller 1993 reference, replace "158-467-474" with -- 158:467-474 --; and within the Purves et al. reference, replace "NeuRosci." with -- Neurosci. --;

<u>Column 1,</u>
Line 29, replace "de novo" with -- *de novo* --;

<u>Column 2,</u>
Line 9, replace "in vivo" with -- *in vivo* --;
Line 24, replace "kal" with -- kαl --
Line 40, replace "de novo" with -- *de novo* --;

<u>Column 3,</u>
Lines 11 and 12, replace "in vivo" with -- *in vivo* --;

<u>Column 5,</u>
Line 15, replace "in vivo" with -- *in vivo* --;

<u>Column 6,</u>
Line 55, replace "N.C." with -- NC --;
Line 61, replace "In Situ" with -- *In Situ* --;
Line 62, replace "In situ" with -- *In situ* --;

<u>Column 7,</u>
Line 37, replace "in vitro" with -- *in vitro* --;
Line 56, replace "Ogalactosidase" with -- βgalactosidase --;

<u>Column 8,</u>
Line 8, replace "untranslated." with -- translated --;

<u>Column 10,</u>
Line 7, replace "in vivo" with -- *in vivo* --;

UNITED STATES PATENT AND TRADEMARK OFFICE
CERTIFICATE OF CORRECTION

PATENT NO.    : 6,309,876 B1
DATED         : October 30, 2001
INVENTOR(S)   : Freda Diane Miller, Andrew Gloster, Grace Causing and Jean George Toma It is certified that error appears in the above-identified patent and that said Letters Patent is hereby corrected as shown below:

Column 12,
Line 24, replace "SV40T" with -- SV40 T --;
Line 36, replace "examined" with -- examined. --;

Column 13,
Line 45, replace "in situ" with -- *in situ* --;
Line 48, replace "A-galactosidase-positive" with -- β-galactosidase-positive --
Line 65, replace "(FIG. 2*f*)," with -- FIG. 2f), --;

Column 14,
Line 38, replace "in vivo" with -- *in vivo* --;
Line 43, replace "in vitro" with -- *in vitro* --; and Column 15,
Line 8, replace "in vivo" with -- *in vivo* --.

Signed and Sealed this

Twentieth Day of August, 2002

*Attest:*

JAMES E. ROGAN
*Attesting Officer*     *Director of the United States Patent and Trademark Office*